United States Patent
Wu et al.

(10) Patent No.: US 7,276,631 B2
(45) Date of Patent: Oct. 2, 2007

(54) CYCLOPENTYLAMINE AND CYCLOHEXYLAMINE DERIVATIVES AS NK-1/SSRI ANTAGONISTS

(75) Inventors: Yong-Jin Wu, Madison, CT (US); Huan He, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 198 days.

(21) Appl. No.: 11/183,700

(22) Filed: Jul. 18, 2005

(65) Prior Publication Data

US 2006/0019944 A1    Jan. 26, 2006

Related U.S. Application Data

(60) Provisional application No. 60/589,716, filed on Jul. 20, 2004.

(51) Int. Cl.
C07C 243/00    (2006.01)
A01N 31/00     (2006.01)

(52) U.S. Cl. ............. 564/462; 514/508; 514/712; 514/716; 514/719; 514/724; 564/453; 564/501; 548/400; 546/184

(58) Field of Classification Search ............ 514/508, 514/712, 716, 719, 724; 564/453, 462, 501; 546/184; 548/400
See application file for complete search history.

(56) References Cited

U.S. PATENT DOCUMENTS 6,136,824 A    10/2000    MacLeod et al.

FOREIGN PATENT DOCUMENTS

WO    WO 2004/005255    1/2004
WO    WO 2004/005256    1/2004

OTHER PUBLICATIONS

Kramer, Mark S., et al., "Distinct Mechanism for Antidepressant Activity by Blockade of Central Substance P Receptors", *Science*, 281 (1998) 1640-1645.

Maubach, Karen A., et al., "Novel Strategies for Pharmacotherapy of Depression", *Current Opinion in Chemical Biology*, 3 (1999) 481-488.

Rosen, Terry J., et al., "Synthesis and Structure-Activity Relationships of CP-122,721, A Second-Generation NK-1 Receptor Antagonist", , *Bioorganic & Medicinal Chemistry Letters*, 8 (1998) 281-284.

Ryckmans, Thomas, et al., "First Dual $NK_1$ Antagonists-Serotonin Reuptake Inhibitors: Synthesis and SAR of a New Class of Potential Antidepressants", *Bioorganic & Medicinal Chemistry Letters*, 12 (2002) 261-264.

*Primary Examiner*—Johann Richter
*Assistant Examiner*—Yate K Cutliff
(74) *Attorney, Agent, or Firm*—Aldo A. Algieri

(57)    ABSTRACT

The present disclosure relates to chemical compounds and their use in human therapy. A specific embodiment of the disclosure relates to compounds of Formula (I); or an isomer, a pharmaceutically acceptable salt or solvate thereof or a pharmaceutically acceptable formulation comprising said compounds

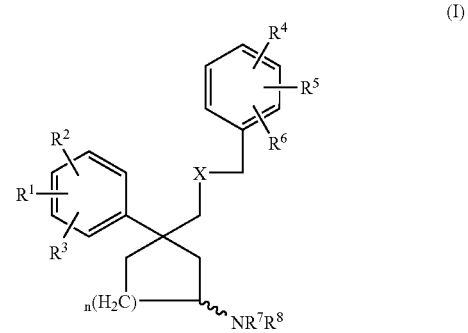

are useful for the useful for the treatment or prevention of conditions mediated by tachykinins and/or selective inhibition of serotonin reuptake transporter protein. The compounds act as dual NK-1 antagonists and selective serotonin reuptake inhibitors.

13 Claims, No Drawings

CYCLOPENTYLAMINE AND CYCLOHEXYLAMINE DERIVATIVES AS NK-1/SSRI ANTAGONISTS

CROSS-REFERENCE TO RELATED APPLICATIONS

This is a non-provisional application which claims the benefit of U.S. Provisional Application No. 60/589,716 filed Jul. 20, 2004.

FIELD OF DISCLOSURE

The present application relates to novel chemical compounds and to the use of such compounds in the treatment of various disorders. A particular embodiment relates to cyclopentylamine and cyclohexylamine derivatives and to pharmaceutical compositions comprising said derivatives useful for the treatment of conditions mediated by tachykinins and/or selective inhibition of serotonin reuptake transporter protein.

BACKGROUND OF THE DISCLOSURE

Depression is a debilitating disease causing significant mortality and affecting up to ten percent of the population. Selective serotonin reuptake inhibitors (SSRI's) have proven to be effective in treating depression, but have the disadvantages of delayed onset of antidepressant activity, limited efficacy and significant side effects. See Novel strategies for pharmacotherapy of depression, K. A. Maubach, N. M. J. Rupniak, M. S. Kramer, and R. G. Hill, *Current Opinion in Chemical Biology* 1999, 3, 491-499. Another class of clinically effective antidepressants are substance P (SP) antagonists which show high affinity and selectivity for the neurokinin 1 (NK-1) receptor. Robust antidepressant activity has been reported for two NK-1 antagonists, MK-869 (M. S. Kramer, et al., *Science* 1998, 281 1640) and CP-122,721 (T. J. Rosen, et al., *Bioorganic and Medicinal Chemistry Letters* 1998, 8, 28 and *CNS Drug News*, December, 2000, 24). NK-1 antagonists offer an alternative approach for treating depression in patients that respond poorly to the SSRI's and other available drugs.

The first dual NK-1 antagonists-serotonin reuptake inhibitors were described by Ryckmans et al. (*Bioorganic and Medicinal Chemistry Letters* 2002, 12, 261-264). Ryckmans discloses phenoxy acetamides and phenyl propionamides as NK-1 antagonists and serotonin reuptake inhibitors and the potential of a new generation of antidepressants.

U.S. Pat. No. 6,136,824 discloses piperidinyl-propane-2-derivatives which exhibit both NK-1 receptor antagonism and/or selective serotonin reuptake inhibitor (hereinafter referred to as SSRI) activity.

International Application WO2004/005256 discloses cyclic amine derivatives that exhibit both NK-1 receptor antagonism and/or SSRI activity.

International Application WO2004/005255 discloses N-benzyl-3-phenyl-3-heterocycylic-propionamide compounds as tachykinin and/or serotonin reuptake inhibitors The compounds of the present disclosure have activity as NK-1 antagonists and/or also have activity as selective serotonin reuptake inhibitors and are thus of use in the treatment of conditions mediated by tachykinins and/or selective inhibition of the serotonin reuptake transporter protein. One aspect of the class of compounds of the present disclosure exhibit both NK-1 receptor antagonist and SSRI activity. Thus, novel dual NK-1 antagonists and SSRI inhibitors effective for the treatment of numerous disorders, such as central nervous system disorders, would be advantageous.

SUMMARY

A class of compounds is provided that are dual NK-1 antagonists and/or serotonin reuptake inhibitors of Formula (I)

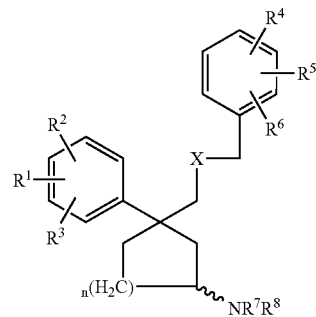

(I)

or an isomer, or a pharmaceutically acceptable salt or solvate thereof wherein $R^1$, $R^2$, $R^3$, $R^4$, $R^5$ and $R^6$ are independently H, $C_{1-4}$ alkyl, $C_{1-4}$ alkoxy, fluoro $C_{1-4}$ alkyl, halo or cyano;

n is an integer from 1 to 2;

X is O, S or $NR^9$;

$R^7$ and $R^8$ each are independently H, $C_{1-5}$ alkyl, $C_{1-4}$ alkoxy $C_{1-4}$ alkyl, $C_{3-6}$ cycloalkyl, or $C_{3-6}$ cycloalkylmethyl; or $R^7$ and $R^8$ together with the nitrogen to which they are attached form a cyclic ring selected from pyrrolidine, piperidine, homopiperidine, piperazine and N-methyl piperazine; and $R^9$ is H or $C_{1-4}$ alkyl.

The present compounds antagonize NK-1 receptors, that is; they bind to the receptors such that Substance P and other tachykinins are inhibited from binding to the NK-1 receptors. The instantly recited compounds are useful as therapeutic agents in conditions characterized by excessive Substance P and other tachykinins expression, and thus, this disclosure provides methods of treating a subject afflicted with such a disorder. The present compounds are also useful as selective inhibitors of serotonin reuptake transporter protein.

DETAILED DESCRIPTION

The compounds of the present disclosure are useful in the treatment of central nervous system disorders and a myriad of other conditions by virtue of their activity as NK-1 receptor antagonists and/or their activity as selective serotonin reuptake inhibitors.

A compound of Formula (I)

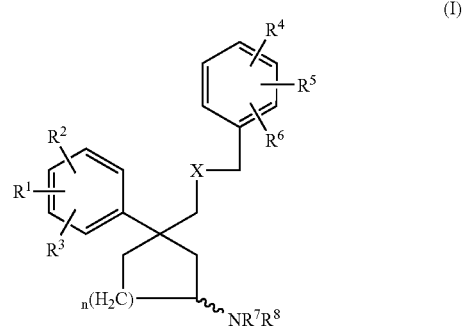

(I)

or an isomer, a pharmaceutically acceptable salt or solvate thereof wherein $R^1$, $R^2$, $R^3$, $R^4$, $R^5$ and $R^6$ are independently H, $C_{1-4}$ alkyl, $C_{1-4}$ alkoxy, fluoro $C_{1-4}$ alkyl, halo or cyano;

n is an integer from 1 to 2;

X is O, S or $NR^9$;

$R^7$ and $R^8$ each are independently H, $C_{1-5}$ alkyl, $C_{1-4}$ alkoxy $C_{1-4}$ alkyl, $C_{3-6}$ cycloalkyl or $C_{3-6}$ cycloalkylmethyl; or $R^7$ and $R^8$ together with the nitrogen to which they are attached form a cyclic ring selected from pyrrolidine, piperidine, homopiperidine, piperazine and N-methyl piperazine; and $R^9$ is H or $C_{1-4}$ alkyl.

"Alkyl" means saturated carbon chains, branched or unbranched having the specified number of carbons. The term "$(C_x-C_y)$ alkyl" where x and y are integers means an alkyl group having from x to y carbon atoms. The term "$C_{1-4}$ alkyl" means an alkyl group having from 1 to 4 carbon atoms and includes, without limitation groups such as methyl, ethyl, n-propyl, isopropyl, methylpropyl, n-butyl, t-butyl, isobutyl and sec-butyl. Derived expressions such as $C_{1-4}$ alkoxy are to be construed accordingly. Alkoxy means an alkyl group of indicated number of carbon atoms attached through an oxygen bridge.

The term "$C_{3-6}$ cycloalkyl" as used herein means a carbon cyclic ring system having from 3 to 6 carbon atoms and includes cyclopropyl, cyclobutyl, cyclopentyl, cyclohexyl and the like. The term "fluoro $C_{1-4}$ alkyl" means a $C_{1-4}$ group in which one or more (in particular 1-3) hydrogen atoms have been replaced by fluorine atoms and includes without limitation trifluoromethyl, fluoromethyl, trifluoromethylethyl, trifluoromethylpropyl and the like.

"Halo" or "halogen" as used herein includes fluorine, chlorine, bromine, and iodine.

References hereinafter to a compound according to the present disclosure include both compounds of formula (I) and their pharmaceutically acceptable salts and solvates. The solvates may for example be hydrates.

Preferably X is oxygen.

Preferably n is 1 or 2.

Preferably $R^7$ is $CH_3$ and $R^8$ is hydrogen.

In another embodiment of the present disclosure are provided compounds of Formula (I) wherein both $R^7$ and $R^8$ are $CH_3$.

In yet another embodiment of the present disclosure are provided compounds of Formula (I) wherein both $R^7$ and $R^8$ are hydrogen.

In another preferred embodiment, $R^4$ and $R^5$ are each $CH_3$ and $R^6$ is H.

In yet another preferred embodiment of the present disclosure $R^4$ and $R^5$ are each $CF_3$ and $R^6$ is H.

According to another embodiment of the present disclosure are provided compounds of Formula (I) wherein $R^4$ is $CF_3$ and $R^5$ and $R^6$ are each H.

Specific compounds of the present disclosure are:

3-((3,5bis(trifluoromethyl)benzyloxy)methyl)-N,N-dimethyl-3-phenylcyclopentanamine;

3-((3,5-bis(trifluoromethyl)benzyloxy)methyl)-N-(2-methoxyethyl)-N-methyl-3-phenylcyclopentanamine;

(1S,3S)-3-((3,5-bis(trifluoromethyl)benzyloxy)methyl)-3-phenylcyclopentanamine;

1-(3-((3,5-bis(trifluoromethyl)benzyloxy)methyl)-3-phenylcyclopentyl)piperidine;

1-(3-((3,5-bis(trifluoromethyl)benzyloxy)methyl)-3-phenylcyclopentyl)pyrrolidine;

3-((3,5-bis(trifluoromethyl)benzyloxy)methyl)-N-cyclopropyl-3-phenylcyclopentanamine;

(1S,3R)-3-((3,5-bis(trifluoromethyl)benzyloxy)methyl)-3-phenylcyclopentanamine;

(1R,3S)-3-((3,5-bis(trifluoromethyl)benzyloxy)methyl)-3-phenylcyclopentanamine; and (1R,3R)-3-((3,5-bis(trifluoromethyl)benzyloxy)methyl)-3-phenylcyclopentanamine.

As the compounds of the present disclosure possess asymmetric carbon atoms, the present invention includes all "isomers" which means all possible stereoisomers, geometric isomers, diastereoisomers, enantiomers, anomers and optical isomers of the compounds of Formula I as described herein and in the claims. The use of a single designation such as (R) or (S) is intended to include mostly one stereoisomer at the position indicated. The use of a double designation such as (R, R), (S, S), (R, S) and (S, R) is intended to include mostly one stereoisomer at the two positions indicated, e.g., (1S,3S) in one specific embodiment. Mixtures of isomers can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The possible enantiomeric forms may also be separated by fractionation through chiral high pressure liquid chromatography columns.

The compounds may exist in the form of pharmaceutically acceptable salts. Such salts may include addition salts with inorganic acids such as, for example, hydrochloric acid and sulfuric acid, and with organic acids such as, for example, acetic acid, citric acid, methanesulfonic acid, toluenesulfonic acid, tartaric acid and maleic acid. Further, in case the compounds contain an acidic group, the acidic group may exist in the form of alkali metal salts such as, for example, a potassium salt and a sodium salt; alkaline earth metal salts such as, for example, a magnesium salt and a calcium salt; and salts with organic bases such as a triethylammonium salt and an arginine salt. In the case of a sublingual formulation a saccharin salt or maleate salt may be of particular benefit. The compounds may be hydrated or non-hydrated.

As described in International Applications WO 2004/005255 and WO 2004/005256 by virtue of their activity as tachykinin (especially NK-1 receptor) antagonists, the compounds of formula (I) are of value in the treatment of a wide variety of clinical conditions which are characterized by the presence of an excess tachykinin, in particular, substance P activity.

As previously stated, the instant compounds are useful in the treatment of central nervous system disorders, particularly in the treatment or prevention of depression and/or in the treatment of anxiety.

Depression includes, but, is not limited to Major Depressive Disorders (MDD), including bipolar depression, unipolar depression, single or recurrent major depressive episodes, recurrent brief depression, catatonic features, melancholic features including feeding disorders, such as anorexia, weight loss, atypical features, anxious depression, or postpartum onset.

Other central nervous system disorders encompassed within the term MDD include neurotic depression, post-traumatic stress disorders (PTSD) and social phobia; dementia of the Alzheimer's type, with early or late onset, with depressed mood; vascular dementia with depressed mood;

mood disorders and tolerance induced by drugs such as alcohol, amphetamines, cocaine, inhalants, opioids, sedatives, anxiolytics and other substances; schizoaffective disorder of the depressed type; and adjustment disorder with depressed mood.

Compounds of the disclosure are also useful in the treatment or prevention of schizophrenic disorders including paranoid schizophrenia, disorganized schizophrenia, catatonic schizophrenia, undifferentiated schizophrenia, residual schizophrenia.

The term anxiety includes, but is not limited to disorders, such as panic disorders, agoraphobia, phobias, obsessive-compulsive disorder, stress disorders including post-traumatic stress disorders, generalized anxiety disorders, acute stress disorders and mixed anxiety-depression disorders.

Compounds of the disclosure are also useful in the treatment or prevention of the cognitive disorders. Cognitive disorders include dementia, amnesia disorders and cognitive disorders not otherwise specified.

Furthermore, the instant compounds are also useful as memory and/or cognition enhancers in healthy humans with no cognitive and/or memory deficit.

In addition, the compounds are useful as analgesics. In particular, they are useful in the treatment of traumatic pain such as postoperative pain; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain; pain of bodily origin; gastrointestinal pain; sport's injury pain; dysmennorrhoea; menstrual pain; meningitis; musculoskeletal pain; low back pain e.g. spinal stenosis; prolapsed disc; sciatica; angina; ankylosing spondyolitis; gout; burns; scar pain; itch and thalamic pain such as post stroke thalamic pain.

Compounds of the disclosure are also useful in the treatment of sleep disorders including insomnia, sleep apnea, narcolepsy, and circadian rhymic disorders.

The instant compounds are also useful as anti-inflammatory agents. In particular, they are useful in the treatment of inflammation in asthma, influenza and chronic bronchitis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the disclosure are also useful in the treatment of allergic disorders, in particular allergic disorders of the skin such as urticaria, and allergic disorders of the airways such as rhinitis.

Compounds of the disclosure are also useful in the treatment of emesis, i.e. nausea, retching and vomiting. Emesis includes acute emesis and anticipatory emesis. The compounds are useful in the treatment of emesis however induced. For example, emesis may be induced by drugs such as cancer chemotherapeutic agents such as alkylating agents, e.g. cyclophosphamide and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; increased intercranial pressure; decreased intercranial pressure (e.g. altitude sickness); opioid analgesics, such as morphine; and gastro-oesophageal reflux disease (GERD) such as erosive GERD and symptomatic GERD or non-erosive GERD, acid indigestion, over-indulgence of food or drink, acid stomach, sour stomach, heartburn, such as episodic heartburn, nocturnal heartburn, and meal-induced heartburn, dyspepsia and functional dyspepsia.

The compounds of the disclosure are also useful in premenstrual dysphoric disorder (PMDD), in chronic fatigue syndrome and multiple sclerosis.

A compound is provided of formula (I) or a pharmaceutically acceptable salt or solvate thereof for use in therapy, in particular in human medicine.

There is also provided as an additional aspect of the disclosure the use of a compound of formula (I) or a pharmaceutically acceptable salt or solvate thereof in the treatment of conditions mediated by tachykinins (including substance P and other neurokinins) and/or by selective inhibition of the serotonin reuptake transporter protein.

In further aspect there is provided the use of a compound of formula (I) or a pharmaceutically acceptable salt or solvate thereof in the preparation of a medicament for use in the treatment of central nervous system disorders, such as depression and/or anxiety.

In an alternative or further aspect there is provided a method for the treatment of a mammal, including man, in particular, in the treatment of conditions mediated by tachykinins, including substance P and other neurokinins and/or by selective inhibition of the serotonin reuptake transporter protein comprising administration of an effective amount of a compound of formula (I) or a pharmaceutically acceptable salt thereof.

In a further aspect of the disclosure there is provided a method for the treatment of a mammal, including man, of depression and/or anxiety which method comprises administration of an effective amount of a compound of formula (I) or a pharmaceutically acceptable salt or solvate thereof.

The instant compounds can be administered in such oral dosage forms as tablets, capsules (each of which includes sustained release or timed release formulations), pills, powders, granules, elixirs, tinctures, suspensions, syrups and emulsions. The compounds may also be administered intravenously, intraperitoneally, subcutaneously, or intramuscularly, all using dosage forms well known to those skilled in the pharmaceutical arts. The compounds can be administered alone, but generally will be administered with a pharmaceutical carrier selected upon the basis of the chosen route of administration and standard pharmaceutical practice. Compounds of this disclosure can also be administered in intranasal form by topical use of suitable intranasal vehicles, or by transdermal routes, using transdermal skin patches. When compounds of this disclosure are administered transdermally the dosage will be continuous throughout the dosage regimen.

The dosage and dosage regimen and scheduling of the instant compound must in each case be carefully adjusted, utilizing sound professional judgment and considering the age, weight and condition of the recipient, the route of administration and the nature and extent of the disease condition. In accordance with good clinical practice, it is preferred to administer the instant compounds at a concentration level which will produce effective beneficial effects without causing any harmful or untoward side effects.

The compounds may be synthesized according to the general schemes provided below. Variables provided in the scheme below are defined in accordance with the description of compounds of the above Formulae unless otherwise specified.

The synthesis of compounds of formula Ia wherein X is O is shown in Scheme 1. The 1,3-diketone 2 was converted to its methyl enol ether 3 by treatment with methyl iodide in the presence of a base such as sodium hydride. Addition of appropriately substituted phenyl magnesium bromide or chloride to 3 provided α,β-unsaturated ketone 4, which underwent 1,4-conjugated addition with hydrogen cyanide to furnish cyano-ketone 5. Ketalization of 5 was achieved with ethylene glycol in the presence of a acid catalyst, and the resulting ketal was reduced with di-isobutylaluminum hydride to give aldehyde 7. This aldehyde was further reduced with sodium hydride to afford alcohol 8, which was converted to 9 by treatment with sodium hydride and appropriately substituted benzyl bromide. The conversion of 9 to ketone 10 was carried out under acidic conditions such as hydrochloric acid in THF. Compounds of formula Ia was prepared from 10 using reductive alkylation reactions, preferably with the two-step procedures: imine formation using Titanium(IV) isopropoxide and reduction of the imine with sodium borohydride (R. J. Mattson, et. al. Bioorg. Med. Chem. Lett. 2003, 13, 1199-1202).

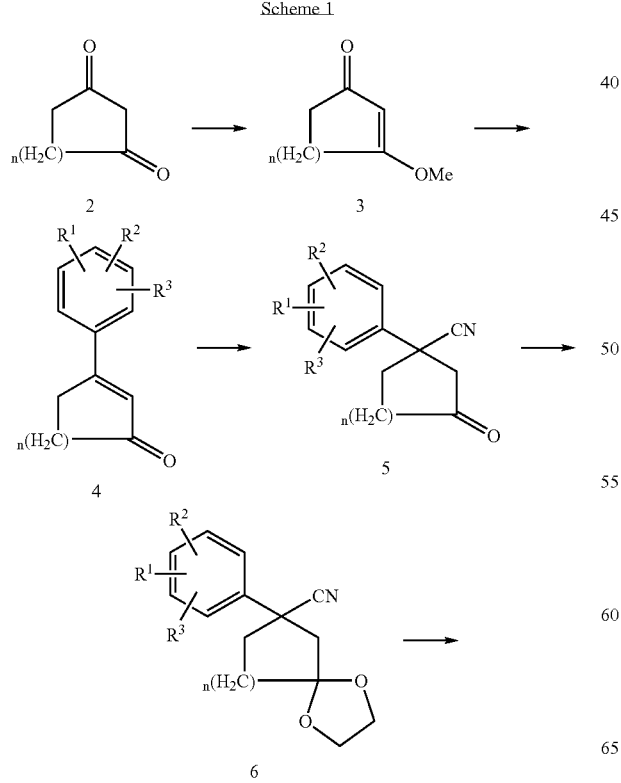

Scheme 1

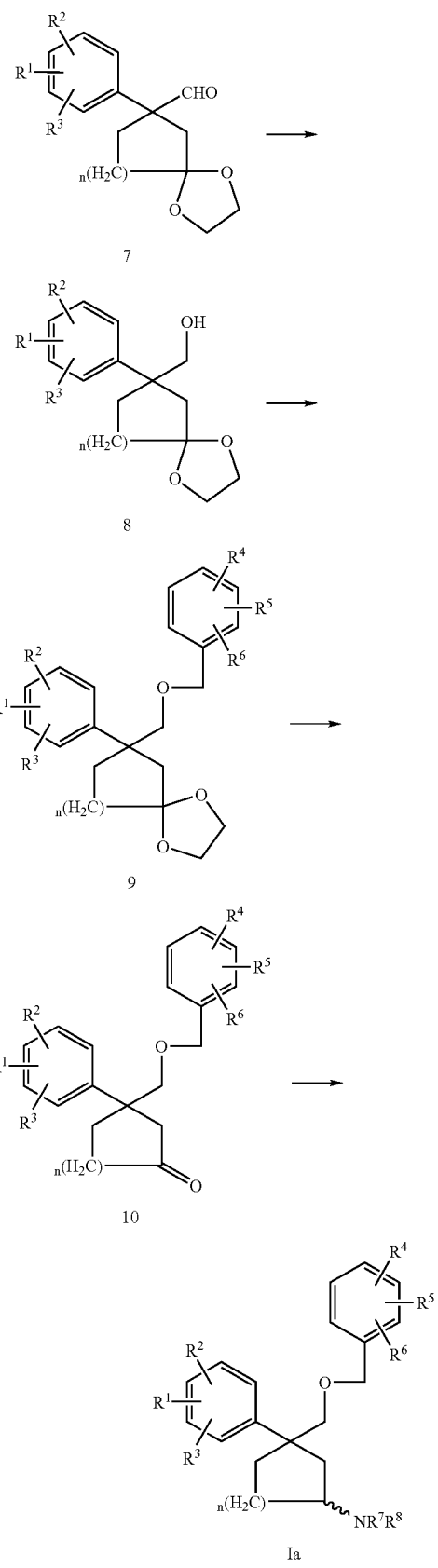

Scheme 2 describes the synthesis of compounds of formula Ib wherein X is $NR^9$. Aldehyde 7 from Scheme 1 underwent reductive alkylation with appropriately substituted benzylamine to provide 12. The conversion of 12 to Ib was carried out in a similar manner to that of 9 to Ia as shown in Scheme 1.

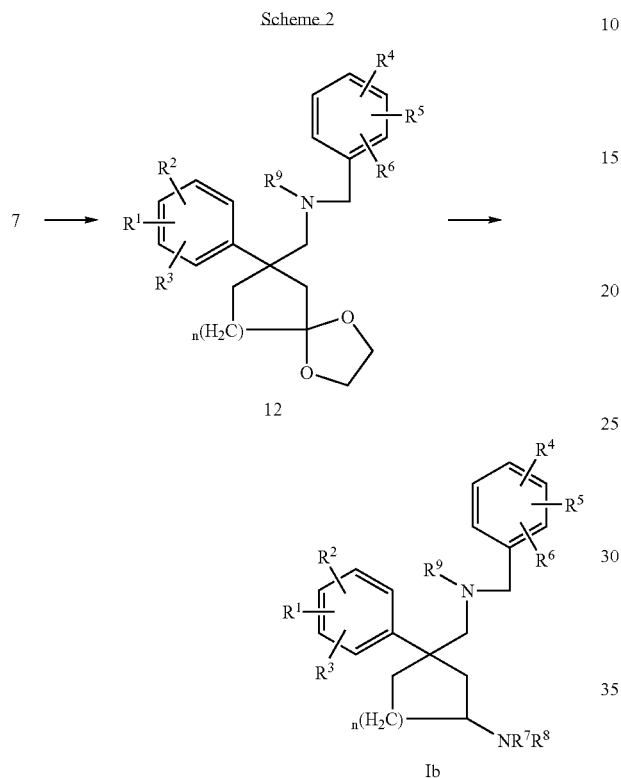

Scheme 3 depicts the synthesis of compounds of formula Ic wherein X is a sulfur atom. Alcohol 7 from Scheme 1 was converted to 14 wherein Y is a mesyl group or tosyl group by treatment with mesyl chloride or tosyl chloride, respectively, in the presence of a base such as triethylamine. Exposure of 14 with appropriately substituted benzylthiol provided compounds of formula 15. The conversion of 15 to Ic was carried out in a similar manner to that of 9 to Ia as shown in Scheme 1.

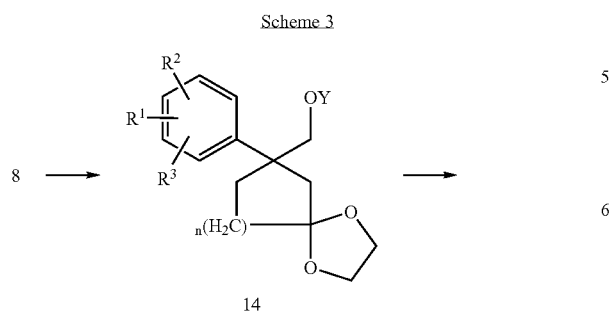

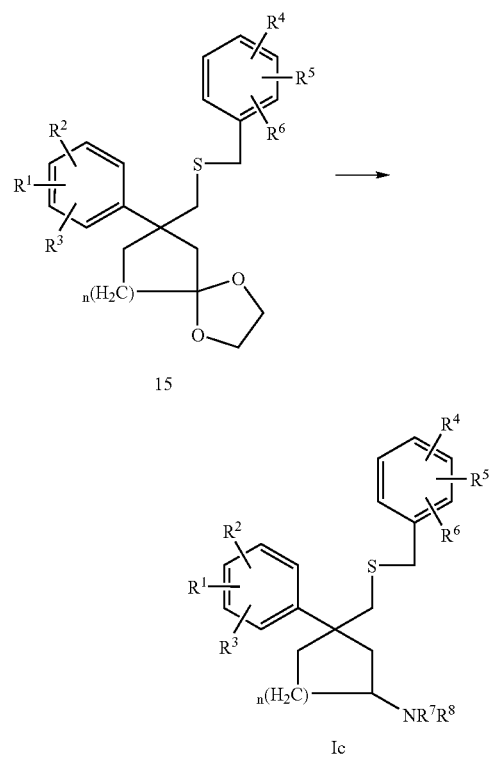

Scheme 4 describes an alternative synthesis of compounds of formula Id wherein X is oxygen and n is 1. Ester 17 was treated with sodium hydride and allyl bromide to give olefin 18, which underwent ring-closing metathesis (R. H. Grubbs and S. Chang, Tetrahedron, 1998, 54, 4413-4450, T. M. Trnka and R. H. Grubbs, Acc. Chem. Res. 2001, 34, 18-29) to provide cyclopentene 19. Reduction of 19 with lithium aluminum hydride gave alcohol 20, which was treated with sodium hydride and appropriately substituted benzylbromide to furnish 21. This compound was converted to alcohol 22 via hydroboration-oxidation (D. H. Hodgson et. al. Tetrahedron, 1999, 55, 10815-10834), and the hydroxyl group in 22 was oxidized to give ketone 23 using pyridinium chlorochromate. Compounds of formula Id were obtained from 23 using reductive alkylation, preferably with two-step procedures: imine formation using Titanium(IV) isopropoxide and reduction of the imine with sodium borohydride (R. J. Mattson, et. al. Bioorg. Med. Chem. Lett. 2003, 13, 1199-1202).

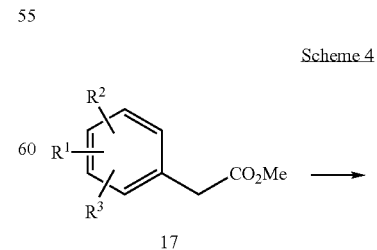

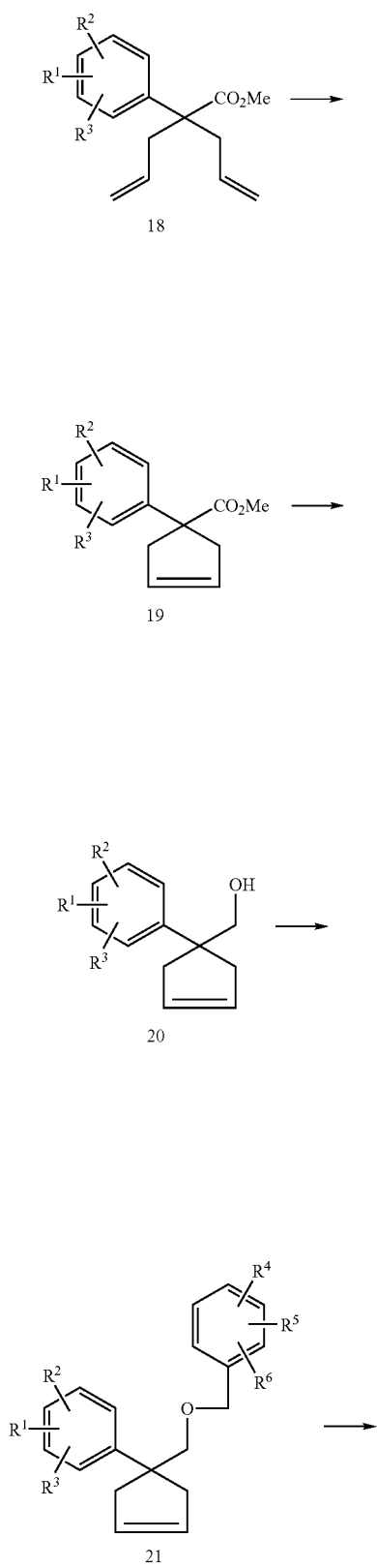
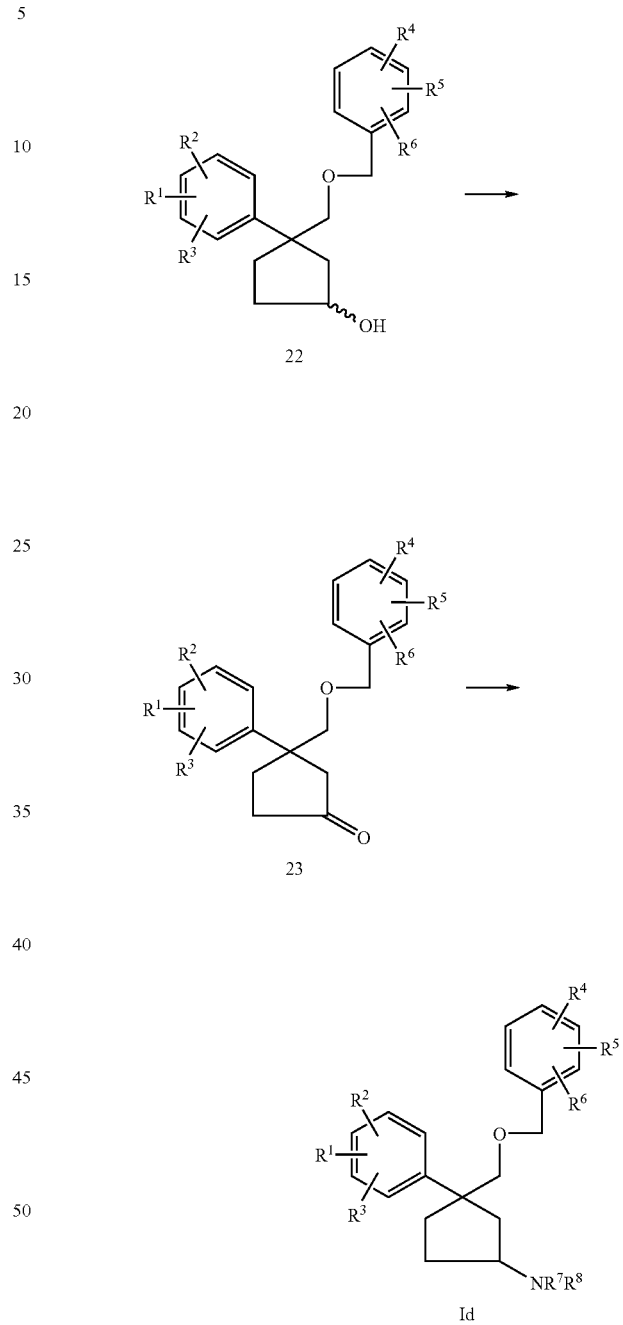

Scheme 5 describes the synthesis of compounds of formula Id from 22. Mitsunobo reaction of 22 with phthalimide (T. A. Shepherd et. al., J. Med. Chem. 2002, 45, 2101-2111) gave 24, which was treated with hydrazine to provide 25. Reductive alkylation of 26 with appropriate amines gave compounds of formula Id. Alternatively, compound 22 can be converted to azide 26 via Mitsunobu reaction with diphenyl phosphorazide (A. S. Thompson et. al., J. Org. Chem. 1993, 58, 5886-5888). Azide 26 can be reduced to amine 25 by hydrogenation or triphenylphosphine.

Scheme 5
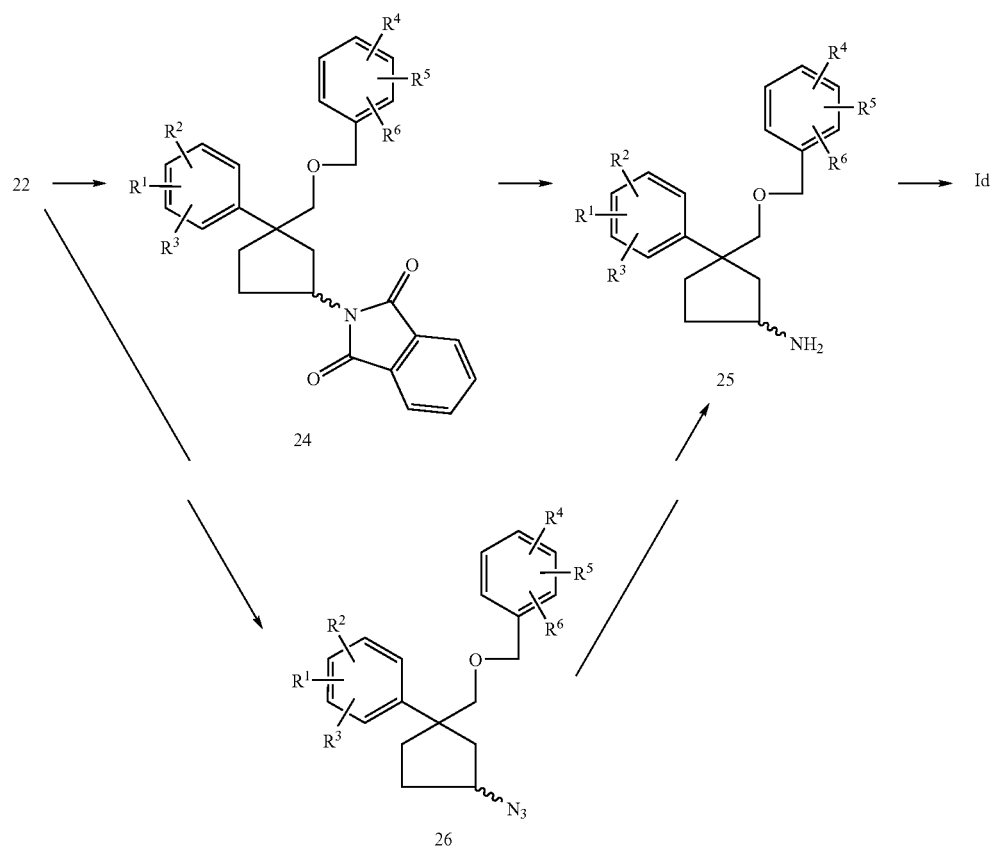
EXAMPLE 1
1-(3-((3,5-Bis(trifluoromethyl)benzyloxy)methyl)-3-phenylcyclopentyl)piperidine
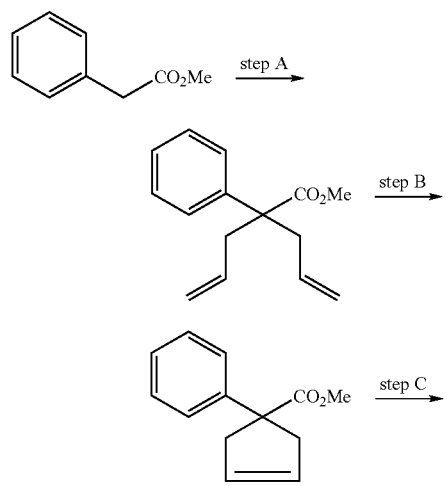
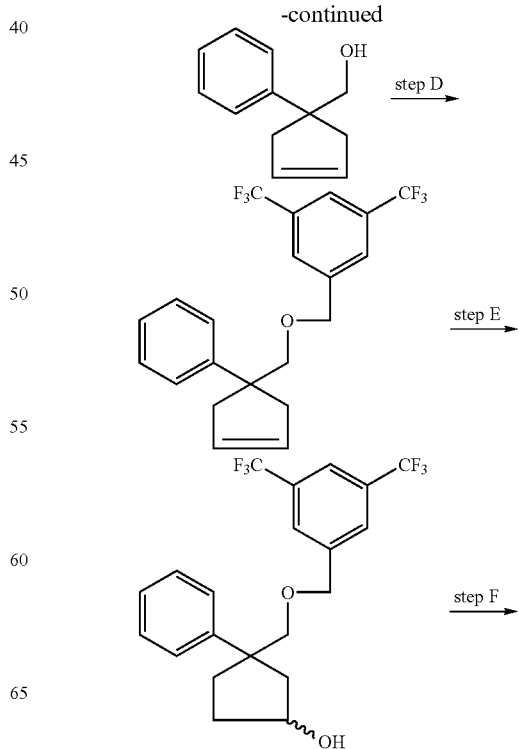

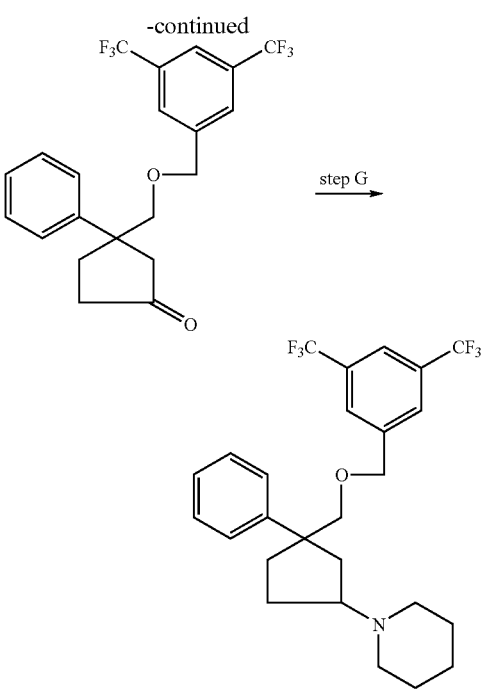

Step A: Methyl 2-allyl-2-phenylpent-4-enoate

To a solution of methyl 2-phenylacetate (500 mg) in DMF (1.0 mL) at 0° C. was added sodium hydride (95% oil dispersion, 210 mg) and the resulting suspension was stirred at 0° C. for 10 min. Allyl bromide (0.72 mL) was added, and the reaction mixture was stirred at room temperature for 30 min. Saturated sodium chloride was added followed by ethyl acetate, the aqueous layer was extracted with ethyl acetate. The combined organic layers were dried over anhydrous sodium sulfate and filtered, and the filtrate was evaporated in vacuo to give the title compound as an oily material (770 mg). $^1$H NMR (400 MHz, CDCl$_3$) δ 2.75 (4H, m), 3.61 (3H, s), 5.01 (4H, m), 5.45 (2H, m), 7.18-7.30 (5H, m).

Step B: Methyl 1-phenylcyclopent-3-enecarboxylate

To a solution of methyl 2-allyl-2-phenylpent-4-enoate (378 mg) in dichloromethane (41 mL) was added benzylidene-bis(tricyclhexylphosphine)dichlororuthenium (68 mg) and the resulting suspension was heated under reflux for 1 h. The solvent was removed in vacuo, and the crude product was purified by preparative TLC eluting with 10% ethyl acetate/90% hexanes to give the title compound as an oil (300 mg). $^1$H NMR (400 MHz, CDCl$_3$) δ 2.74 (2H, d, J=14.8 Hz), 3.40 (2H, d, J=14.8 Hz), 3.63 (3H, s), 5.76 (2H, s), 7.22-7.31 (5H, m). $^{13}$C NMR (100 MHz, CDCl$_3$) δ 42.8, 52.5, 58.4, 126.6, 126.8, 128.7, 129.2, 143.7, and 176.6.

Step C: (1-Phenylcyclopent-3-enyl)methanol

To a solution of methyl 1-phenylcyclopent-3-enecarboxylate (298 mg) in ether (10 mL) at 0° C. was added lithium aluminum hydride (1.0 M solution in ether, 1.48 mL), and the resulting suspension was stirred at 0° C. for 30 min. The reaction was quenched with saturated sodium sulfate and then diluted with ether (100 mL). Anhydrous sodium sulfate was added, and the ether solution was filtered. The filtrate was evaporated in vacuo to give the title compound as an oil (257 mg). $^1$H NMR (400 MHz, CDCl$_3$) δ 2.70 (4H, s), 3.54 (2H, d, J=5.6 Hz), 5.75 (1H, s), 7.22-7.35 (5H, m).

Step D: 1-(((1-Phenylcyclopent-3-enyl)methoxy)methyl)-3,5-bis(trifluoromethyl) benzene To a solution of (1-phenylcyclopent-3-enyl)methanol (257 mg) and 3,5-(bis-trifluoromethyl)benzyl bromide (0.41 mL) in DMF (2.5 mL) at 0° C. was added sodium hydride (95% oil dispersion, 75 mg) and the resulting suspension was stirred at room temperature for 30 min. Water was added followed by ethyl acetate, and the aqueous layer was extracted with ethyl acetate. The combined organic layers were dried over anhydrous sodium sulfate and filtered, and the filtrate was evaporated in vacuo. The residue was purified by preparative TLC eluting with 15% ethyl acetate/85% hexanes to give the title compound as an oily material. $^1$H NMR (400 MHz, CDCl$_3$) δ 2.73 (4H, s), 3.51 (2H, s), 4.44 (2H, s), 5.74 (2H, s), 7.21-7.32 (5H, m), 7.57 (2H, s), and 7.72 (1H, s).

Step E: 3-((3,5-bis(trifluoromethyl)benzyloxy)methyl)-3-phenylcyclopentanol

To a solution of 1-(((1-phenylcyclopent-3-enyl)methoxy)methyl)-3,5-bis(trifluoromethyl)benzene (200 mg) in THF (0.55 mL) at 0° C. was added borane-tetrahydrofuran complex (1.0 M solution, 0.55 mL) dropwise, and the resulting solution was warmed to room temperature and stirred at room temperature for 12 h. The reaction mixture was cooled to 0° C., and water (1.0 mL) was added slowly followed by 30% hydrogen peroxide (0.19 mL) and 1 N sodium hydroxide (0.55 mL). The resulting solution was stirred at room temperature for 5 min, and ethyl acetate (2.0 mL) was added. The aqueous layer was extracted with ethyl acetate, the combined organic layers were dried over anhydrous sodium sulfate and filtered, and the filtrate was evaporated in vacuo. The residue was purified by preparative TLC eluting with 40% ethyl acetate/60% hexanes to give the title compound as an oily material. $^1$H NMR (400 MHz, CDCl$_3$) δ 2.06 (m), 1.9-2.6 (m), 3.42 (s), 3.57 (q, J=8.8 Hz), 4.45 (s), 4.3-4.6 (m), 7.1-7.5 (m), 7.47 (s), 7.64 (s), 7.74 (s), and 7.76 (s).

Step F: 3-((3,5-Bis(trifluoromethyl)benzyloxy)methyl)-3-phenylcyclopentanone To a solution of 3-((3,5-bis(trifluoromethyl)benzyloxy)methyl)-3-phenylcyclopentanol (142 mg) in dichloromethane (10 mL) at room temperature were added pyridinium chlorochromate (146 mg) and powdered 4 A° molecular sieves (146 mg), and the resulting mixture was stirred at room temperature for 1.5 h and then filtered through a small pad of silica gel. The filtrate was evaporated in vacuo and the residue was purified by preparative TLC eluting with 30% ethyl acetate/70% hexanes to give the title compound as an oily material (150 mg). $^1$H NMR (400 MHz, CDCl$_3$) δ 2.3-2.6 (4H, m), 2.68 (1H, d, J=17.6 Hz), 2.76 (1H, d, J=17.6 Hz), 3.52 (1H, q, J=9.2 Hz), 3.58 (1H, d, J=9.2 Hz), 4.52 (2H, s), 7.2-7.4 (5H, m), 7.59 (2H, s), 7.76 (1H, s).

Step G: 1-(3-((3,5-Bis(trifluoromethyl)benzyloxy)methyl)-3-phenylcyclopentyl) piperidine To a solution of 3-((3,5-bis(trifluoromethyl)benzyloxy)methyl)-3-phenylcyclopentanone (5 mg) in THF (0.10 mL)

at room temperature was added piperidine (50 μL) followed by titanium(IV) isopropoxide and the resulting solution was heated at 65° C. in a sealed vial for 2 h. The solution was cooled to room temperature, 100 μL ethanol was added followed by sodium borohydride (4 mg), and the resulting suspension was stirred at room temperature for 1 h. The reaction mixture was then passed through a clean-up extraction column (2 g) and washed with methanol (0.3 mL). The filtrate was evaporated in vacuo, and the residue was purified by preparative TLC eluting with 10% MeOH/1% $NH_3.H_2O$/89% $CH_2Cl_2$ to give the title compound (1.2 mg). $^1$H NMR (400 MHz, CDCl$_3$) δ 1.3-2.5 (m), 3.43 (d, J=8.8 Hz), 3.48 (d, J=8.8 Hz), 3.51 (d, J=8.0 Hz), 3.61 (d, J=8.0 Hz), 4.45 (s), 7.1-7.4 (m), 7.53 (s), 7.58 (s), 7.71 (s), and 7.74 (s). HPLC retention time (1.96 min, method A). MS: 486 (MH$^+$).

Examples 2-6 were prepared following the general procedure shown in Example 1.

EXAMPLE 2

1-(3-((3,5-Bis(trifluoromethyl)benzyloxy)methyl)-3-phenylcyclopentyl)pyrrolidine

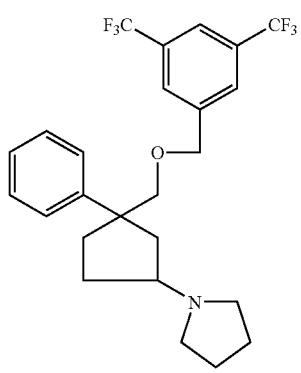

$^1$H NMR (400 MHz, CDCl$_3$) δ 1.3-2.5 (m), 3.45 (d, J=8.8 Hz), 3.49 (d, J=8.8 Hz), 3.60 (m), 3.68 (m), 4.47 (s), 4.49 (s), 7.1-7.4 (m), 7.52 (s), 7.60 (s), 7.71 (s), and 7.75 (s). HPLC retention time (1.94 min, method A). MS: 472 (MH$^+$).

EXAMPLE 3

4-(3-((3,5-bis(trifluoromethyl)benzyloxy)methyl)-3-phenylcyclopentyl)morpholine

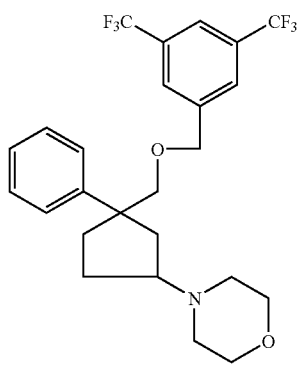

$^1$H NMR (400 MHz, CDCl$_3$) δ 1.3-2.5 (m), 3.43 (d, J=8.8 Hz), 3.49 (d, J=8.8 Hz), 3.51 (d, J=8.0 Hz), 3.60 (d, J=8.0 Hz), 4.46 (s), 7.28 (m), 7.55 (s), 7.57 (s), 7.72 (s), and 7.74 (s). HPLC retention time (1.90 min, method A). MS: 488 (MH$^+$).

EXAMPLE 4

3-((3,5-Bis(trifluoromethyl)benzyloxy)methyl)-N-cyclopropyl-3-phenylcyclopentanamine

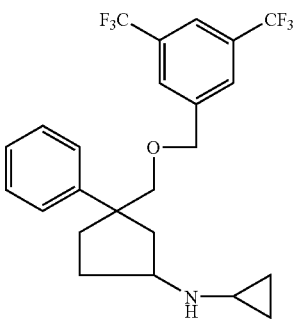

$^1$H NMR (400 MHz, CDCl$_3$) δ 0.86 (m), 1.4-2.2 (m), 2.60 (m), 3.47 (d, J=9.2 Hz), 3.44 (d, J=9.2 Hz), 3.51 (d, J=8.8 Hz), 3.61 (d, J=8.8 Hz), 4.45 (s). 4.47 (s), 7.29 (m), 7.56 (s), 7.73 (s). HPLC retention time (1.96 min, method A). MS: 458 (MH$^+$).

EXAMPLE 5

3-((3,5-bis(trifluoromethyl)benzyloxy)methyl)-N-(2-methoxyethyl)-N-methyl-3-phenylcyclopentanamine

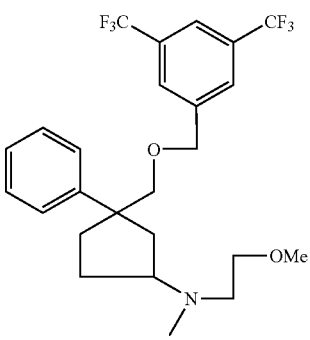

$^1$H NMR (400 MHz, CDCl$_3$) δ 0.86 (m), 1.8-2.7 (m), 3.33 (s), 3.34 (s), 3.42 (d, J 9.2 Hz), 3.47 (d, J=9.2 Hz), 3.53 (m), 3.61 (m), 4.45 (s), 4.47 (s), 7.29 (m), 7.54 (s), 7.57 (s), 7.72 (s), and 7.74 (s). HPLC retention time (1.87 min, method A). MS: 490 (MH$^+$).

EXAMPLE 6
3-((3,5-bis(trifluoromethyl)benzyloxy)methyl)-N,N-dimethyl-3-phenylcyclopentanamine
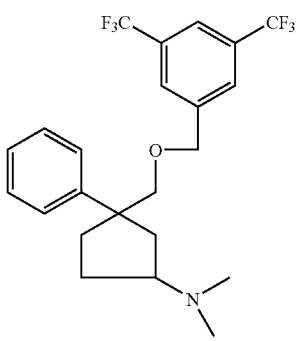
$^1$H NMR (400 MHz, CDCl$_3$) δ 1.5-2.9 (m), 2.24 (s), 2.25 (s), 3.45 (d, J=8.8 Hz), 3.47 (1H, d, J=8.8 Hz), 3.50 (d, J=8.8 Hz), 3.59 (d, J=8.8 Hz), 4.45 (s), 7.2 (m), 7.54 (s), 7.58 (s), 7.72 (s). HPLC retention time (2.06 and 2.37 min, method A). MS: 446 (MH$^+$).
EXAMPLE 7
(1S,3R)-3-((3,5-bis(trifluoromethyl)benzyloxy)methyl)-3-phenylcyclopentanamine
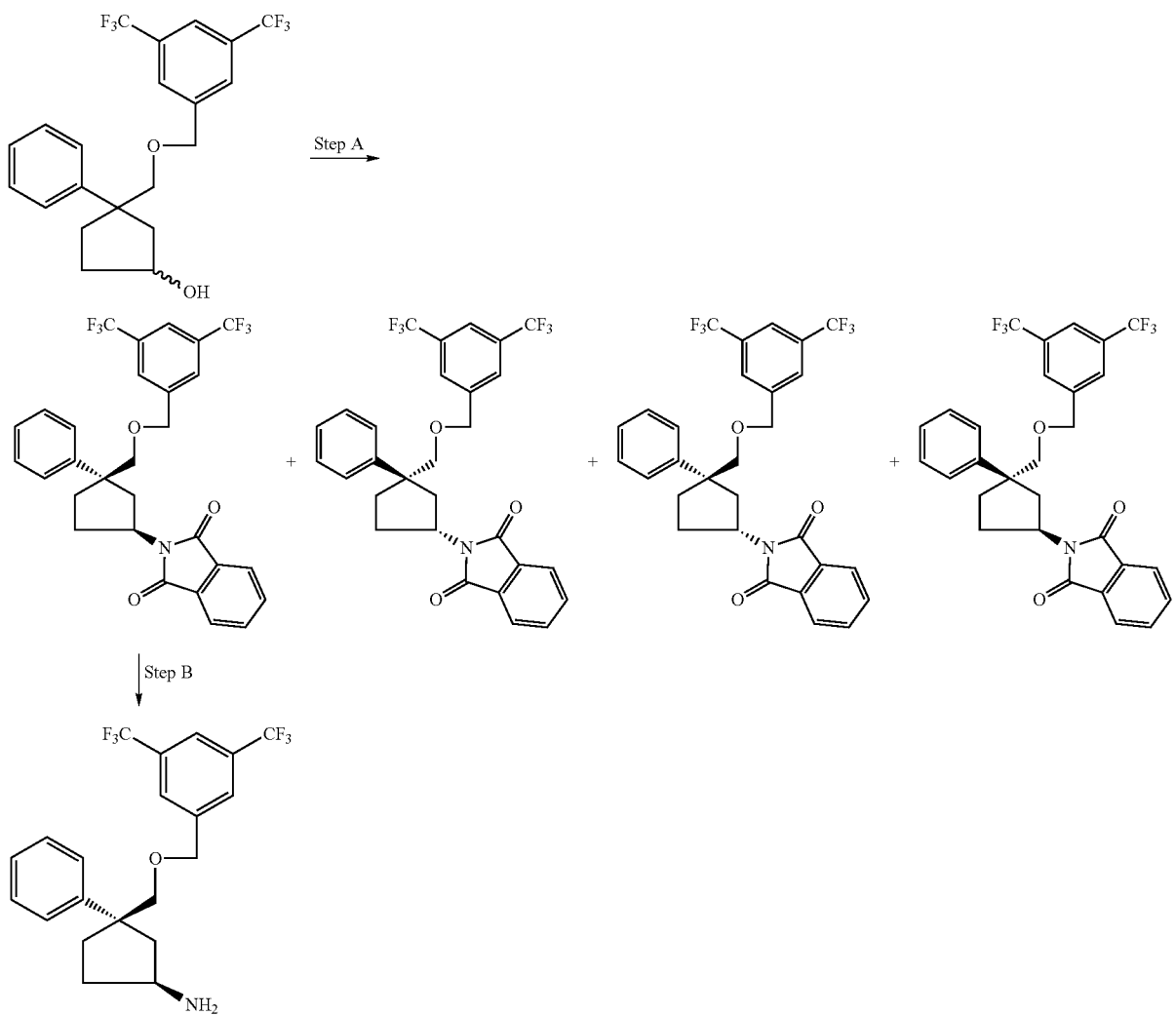

Step A: 2-((1S,3R)-3-((3,5-bis(trifluoromethyl)ben-
zyloxy)methyl)-3-phenylcyclopentyl)isoindoline-1,
3-dione To a solution of tripehnylphosphine (102 mg) in THF (0.20 mL) at 0° C. was added diethyl azodicarboxylate (61 μL) and the resulting solution was stirred at 0° C. for 30 min. Phthalimide (57 mg) was added followed by 3-((3,5-bis(trifluoromethyl)benzyloxy)methyl)-3-phenylcyclopentanol (available from Step E of Example 1) (148 mg) in THF (0.50 mL), and the reaction mixture was stirred at 0° C. for 2 h. The reaction mixture was diluted with ethyl acetate and water was added. The aqueous layer was extracted with ethyl acetate, the combined organic layers were dried over anhydrous sodium sulfate and filtered, and the filtrate was evaporated in vacuo. The residue was purified by preparative TLC eluting with 20% ethyl acetate/80% hexanes to give two products as racemates: 2-((1SR,3RS)-3-((3,5-bis(trifluoromethyl)benzyloxy)methyl)-3-phenylcyclopentyl)isoindoline-1,3-dione (less polar fraction) and 2-((1RS,3RS)-3-((3,5-bis(trifluoromethyl)benzyloxy)methyl)-3-phenylcyclopentyl)isoindoline-1,3-dione (more polar fraction).

2-((1SR,3RS)-3-((3,5-bis(trifluoromethyl)benzyloxy)methyl)-3-phenylcyclopentyl)isoindoline-1,3-dione (210 mg) was separated by preparative chiral HPLC (AD column, 20×250 mm, 95% heptane/5% ethanol, 10 mL/min flow rate) to give two enantiomers: (1S,3R)- and (1R,3S)-2-(3-((3,5-bis(trifluoromethyl)benzyloxy)methyl)-3-phenylcyclopentyl)isoindoline-1,3-dione.

2-((1R,3S)-3-((3,5-bis(trifluoromethyl)benzyloxy)methyl)-3-phenylcyclopentyl)isoindoline-1,3-dione: HPLC retention time: 11.08 min (OJ column, 4.6×250 mm, flow rate 0.8 mL/min, 85% hexanes/15% ethanol). $^1$H NMR (400 MHz, CDCl$_3$) δ 1.97 (1H, m), 2.14 (1H, m), 2.34 (1H, m), 2.51 (3H, m), 3.68 (1H, d, J=8.8 Hz), 3.84 (1H, d, J=8.8 Hz), 4.53 (2H, s), 4.75 (1H, quintet, J=8.8 Hz), 7.24 (2H, m), 7.36 (3H, m), 7.61 (2H, s), 7.69 (3H, m), 7.82 (2H, m). $^{13}$C NMR (CDCl$_3$, 100 MHz) δ 28.59, 34.30, 38.28, 49.94, 51.73, 71.99, 79.50, 121.57, 123.77 (q, J=271 Hz), 123.49, 126.80, 127.15, 127.39, 128.66, 131.85 (q, J=33 Hz), 132.46, 134.33, 141.91, 146.10, and 169.77. HRMS m/z calcd for C$_{29}$H$_{22}$F$_6$NO$_3$ (M–H)$^-$ 546.1504. found 546.1501.

2-((1S,3R)-3-((3,5-bis(trifluoromethyl)benzyloxy)methyl)-3-phenylcyclopentyl) isoindoline-1,3-dione: HPLC retention time: 8.02 min (OJ column, 4.6×250 mm, flow rate 0.8 mL/min, 85% hexanes/15% ethanol). The NMR data is identical as that of (1R,3S) isomer. HRMS m/z calcd for C$_{29}$H$_{22}$F$_6$NO$_3$ (M–H)$^-$ 546.1504. found 546.1489.

2-((1RS,3RS)-3-((3,5-bis(trifluoromethyl)benzyloxy)methyl)-3-phenylcyclopentyl)isoindoline-1,3-dione (180 mg) was separated by preparative chiral HPLC (OJ column, 20×250 mm, 85% heptane/15% ethanol, flow rate 10 mL/min) to give two enantiomers: (1S,3S)-(69 mg) and (1R,3R)-(68 mg) 2-(3-((3,5-bis(trifluoromethyl)benzyloxy)methyl)-3-phenylcyclopentyl)isoindoline-1,3-dione.

2-((1S,3S)-3-((3,5-bis(trifluoromethyl)benzyloxy)methyl)-3-phenylcyclopentyl)isoindoline-1,3-dione: HPLC retention time: 8.43 min (AD column, 4.6×250 mm, flow rate 1 mL/min, 90% hexanes/10% ethanol). $^1$H NMR (CDCl$_3$, 400 MHz) δ 2.2 (3H, m), 2.5 (2H, m), 2.59 (1H, dd, J=10.8, 10.4 Hz), 3.51 (1H, d, J=8.8 Hz), 3.56 (1H, d, J=8.8 Hz), 4.48 (1H, d, J=13.2 Hz), 4.53 (1H, d, J=13.2 Hz), 4.95 (1H, m), 7.31 (5H, m), 7.59 (2H, s), 7.68 (5H, m). $^{13}$C NMR (100 MHz, CDCl$_3$) δ 28.40, 33.82, 38.38, 49.66, 51.45, 71.75, 77.98, 123.32 (q, J=271 Hz), 121.32, 123.09, 126.30, 126.80, 126.99, 128.07, 131.56 (q, J=32 Hz), 132.06, 133.89, 141.23, 146.88, and 168.28. HRMS m/z calcd for C$_{29}$H$_{22}$F$_6$NO$_3$ (M–H)$^-$ 546.1504. found 546.1493.

2-((1R,3R)-3-((3,5-bis(trifluoromethyl)benzyloxy)methyl)-3-phenylcyclopentyl)isoindoline-1,3-dione: HPLC retention time: 7.64 min (AD column, 4.6×250 mm, flow rate 1 mL/min, 90% hexanes/10% ethanol). The NMR data is identical to that of its (1R,3R) isomer. HRMS m/z calcd for C$_{29}$H$_{22}$F$_6$NO$_3$ (M–H)$^-$ 546.1504. found 546.1494.

Step B: (1S,3R)-3-((3,5-bis(trifluoromethyl)benzyloxy)methyl)-3-phenylcyclopentanamine To a solution of 2-((1S,3R)-3-((3,5-bis(trifluoromethyl)benzyloxy)methyl)-3-phenylcyclopentyl)isoindoline-1,3-dione (122 mg) in toluene (0.89 mL) was added anhydrous hydrazine (69 μL), and the reaction mixture was heated at 80° C. for 12 h. The precipitate was removed by filtration, and the filtrate was evaporated in vacuo to give the title compound (88 mg). $^1$H NMR (400 MHz, CDCl$_3$) δ 1.45 (1H, m), 1.66 (2H, broad s), 1.68 (1H, dd, J=7.2, 13.2 Hz), 2.04 (2H, m), 2.20 (1H, m), 2.45 (1H, dd, J=7.6, 13.2 Hz), 3.43 (1H, quintet, J=7.2 Hz), 3.52 (1H, d, J=8.8 Hz), 3.61 (1H, d, J=8.8 Hz), 4.45 (1H, d, J=13.2 Hz), 4.50 (1H, d, J=13.2 Hz), 7.23 (5H, m), 7.58 (2H, s), and 7.73 (1H, s). HRMS m/z calcd for C$_{21}$H$_{22}$F$_6$NO (M+H)$^+$ 418.1607. found 546.1620.

EXAMPLE 8

(1R,3S)-3-((3,5-bis(trifluoromethyl)benzyloxy)methyl)-3-phenylcyclopentanamine

To a solution of 2-((1R,3S)-3-((3,5-bis(trifluoromethyl)benzyloxy)methyl)-3-phenylcyclopentyl)isoindoline-1,3-dione (113 mg), available from Example 7, in toluene (0.83 mL) was added anhydrous hydrazine (66 μL), and the reaction mixture was heated at 80° C. for 12 h. The precipitate was removed by filtration, and the filtrate was evaporated in vacuo to give the title compound (80 mg). The $^1$H NMR data is identical to that of its (1S,3R) isomer shown in Example 6. HRMS m/z calcd for C$_{21}$H$_{22}$F$_6$NO (M+H)$^+$ 418.1607. found 546.1619.

EXAMPLE 9

(1R,3R)-3-((3,5-bis(trifluoromethyl)benzyloxy)methyl)-3-phenylcyclopentanamine

To a solution of 2-((1R,3R)-3-((3,5-bis(trifluoromethyl)benzyloxy)methyl)-3-phenylcyclopentyl)isoindoline-1,3-dione (68 mg), available from Example 7, in toluene (0.50 mL) was added anhydrous hydrazine (41 μL), and the reaction mixture was heated at 80° C. for 12 h. The precipitate was removed by filtration, and the filtrate was evaporated in vacuo to give the title compound (49 mg). $^1$H NMR (CDCl$_3$, 400 MHz) δ 1.46 (1H, m), 1.60 (2H, broad s), 1.74 (1H, dd, J=6.0, 12.8 Hz), 2.09 (2H, m), 2.19 (1H, m), 2.48 (1H, dd, J=6.8, 12.8 Hz), 3.40 (1H, d, J=8.8 Hz), 3.44 (1H, d, J=8.8 Hz), 3.53 (1H, quintet, J=7.2 Hz), 4.43 (2H, s), 7.25 (5H, m), 7.55 (2H, s), and 7.73 (1H, s). HRMS m/z calcd for C$_{21}$H$_{22}$F$_6$NO (M+H)$^+$ 418.1607. found 546.1621.

EXAMPLE 10

(1S,3S)-3-((3,5-bis(trifluoromethyl)benzyloxy)methyl)-3-phenylcyclopentanamine

To a solution of 2-((1S,3S)-3-((3,5-bis(trifluoromethyl)benzyloxy)methyl)-3-phenylcyclopentyl)isoindoline-1,3-dione (69 mg), available from Example 7, in toluene (0.50 mL) was added anhydrous hydrazine (41 μL), and the reaction mixture was heated at 80° C. for 12 h. The precipitate was removed by filtration, and the filtrate was evaporated in vacuo to give the title compound (45 mg). The $^1$H NMR data is identical with that of its (1R,3R) isomer. HRMS m/z calcd for $C_{21}H_{22}F_6NO$ (M+H)$^+$ 418.1607. found 546.1625.

EXAMPLE 11

3-((3,5-bis(trifluoromethyl)benzyloxy)methyl)-N-methyl-3-phenylcyclohexanamine

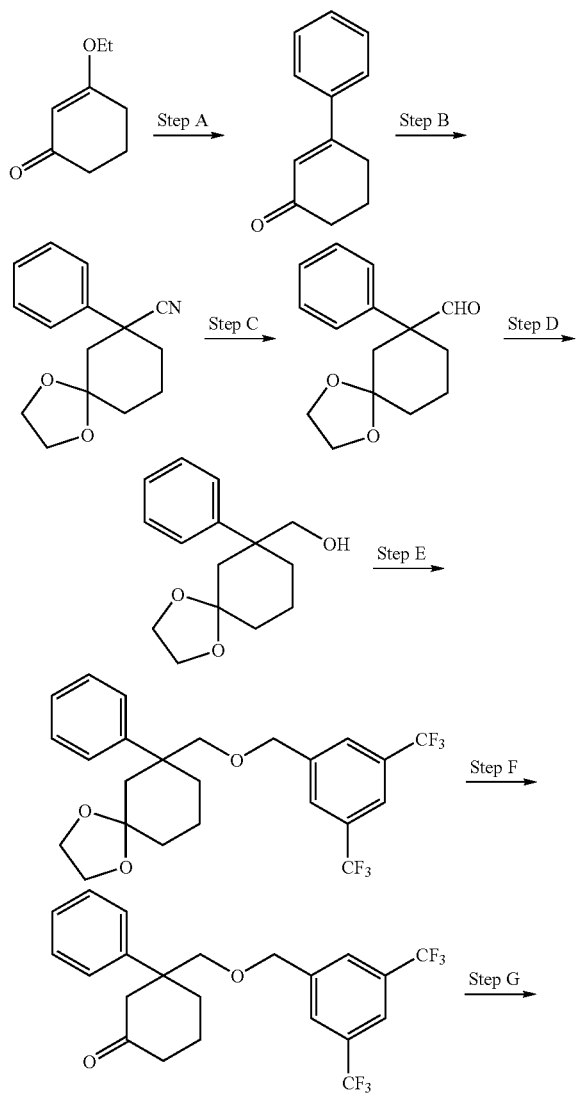

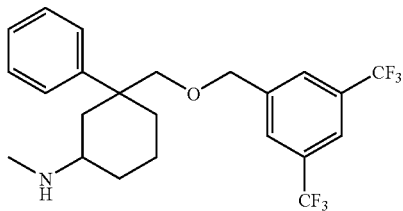

Step A: 3-phenylcyclohex-2-enone

At 0° C., 3-ethoxycyclohex-2-enone (2 g, 14.3 mmol) in THF (2 mL) was added phenylmagnesium bromide (1.0 M solution in THF, 15.0 mL) slowly. After the addition, the reaction mixture was warmed up to room temperature and stirred for 1 hr. Then 1N HCl solution (15.16 mL) was added to quench the reaction and the organic layer was separated. The aqueous layer was extracted with dichloromethane 3 times. The combined organic layers were dried over magnesium sulfate, filtered and concentrated to give the title compound as yellow solid (quantitative yield). $^1$H NMR (400 MHz, CDCl$_3$) δ 2.16 (2H, dt, J=4, 12 Hz), 2.48 (2H, t, J=8 Hz), 2.77 (2H, dt, J=2, 6 Hz), 6.41 (1H, t, J=2 Hz), 7.39-7.41 (3H, m), 7.52-7.54 (2H, m).

Step B: 3,3-ethylenedioxy-1-phenylcyclohexanecarbonitrile

A mixture of 3-phenylcyclohex-2-enone (14.3 mmol), potassium cyanide (1.92 g) and trimethylamine hydrochloride (2.06 g, 21.5 mmol) in H$_2$O (10 mL) and DMF (57 mL) was heated at 93° C. for 6 hr. After cooling down to room temperature, saturated sodium bicarbonate was added and the organic layer was separated. The aqueous layer was extracted with diethyl ether 3 times. The combined organic layers were washed with saturated sodium chloride solution, dried over magnesium sulfate, filtered and concentrated under vacuum to get 2.62 g of the crude 3-oxo-1-phenylcyclohexanecarbonitrile which was directly taken to the next step without further purification.

The mixture of 3-oxo-1-phenylcyclohexanecarbonitrile (2.62 g), ethylene glycol (3.65 mL) and pyridinium p-toluene sulfonate (1 spatula) in benzene (40 mL) was stirred at 111° C. with Dean-Stark apparatus overnight. After cooling down to room temperature, the mixture was washed with saturated sodium bicarbonate and the organic layer was separated. The aqueous layer was extracted with dichloromethane 3 times and the combined organic layers were dried over magnesium sulfate, filtered and concentrated under vacuum. The crude material was purified by Flash Chromatography with from 25% ethyl acetate/75% hexane to 30% ethyl acetate/70% hexane over 20 minutes. The title compound was obtained as a white solid (1.66 g, 48% yield in 2 steps). $^1$H NMR (400 MHz, CDCl$_3$) δ 1.56 (1H, dt, J=4, 16 Hz), 1.70-1.79 (1H, m), 1.89-1.96 (3H, m), 2.06-2.28 (3H, m), 3.89-3.97 (2H, m), 4.03-4.12 (2H, m), 7.28-7.32 (1H, m), 7.36-7.39 (2H, m), 7.48-7.51 (2H, m). HPLC purity (retention time): 95% (1.62 min, method C). MS: 266.37 (M+Na$^+$).

Step C: 3,3-ethylenedioxy-1-phenylcyclohexanecarbaldehyde

At −78° C., 3-ethylenedioxy-1-phenylcyclohexanecarbonitrile (1.66 g, 6.83 mmol) in toluene (20 mL) was added DIBAL-H (1.0 M solution in toluene, 8.88 mL) slowly and was stirred for 1 hr. The reaction mixture was warmed up to room temperature and was added 1N HCl solution (2.60 mL) and was stirred for 1 hr. Saturated sodium bicarbonate was added to quench the reaction and the organic layer was separated. The aqueous layer was extracted with dichloromethane 3 times and the combined organic layers were dried over magnesium sulfate, filtered and concentrated under vacuum. The crude material was purified by filtering through a short silica gel pad with dichloromethane to give the title compound as a white sticky oil (1.43 g, 85% yield). $^1$H NMR (400 MHz, CDCl$_3$) δ 1.32-1.40 (1H, m), 1.46-1.54 (1H, m), 1.72-1.86 (3H, m), 2.08 (1H, d, J=16 Hz), 2.59-2.67 (2H, m), 3.94-4.07 (4H, m), 7.15-7.36 (5H, m), 9.36 (1H, d, J=4 Hz).

Step D: (3,3-ethylenedioxy-1-phenylcyclohexyl)methanol

To a solution of methyl 3,3-ethylenedioxy-1-phenylcyclohexanecarbaldehyde (1.43 g, 5.81 mmol) in methanol (25 mL) at 0° C. was added sodium borohydride (221 mg) in portions, and the resulting suspension was stirred at room temperature overnight. The reaction was quenched with saturated sodium bicarbonate and methanol was removed under vacuum. The aqueous layer was extracted with dichloromethane 3 times. The combined organic layers were dried over magnesium sulfate, filtered and concentrated in vacuo to give the title compound as clear colorless sticky oil (1.25 g, 87% yield). $^1$H NMR (400 MHz, CDCl$_3$) δ 1.48-1.81 (7H, m), 1.88 (1H, d, J=16 Hz), 2.06 (1H, d, J=12 Hz), 2.22 (1H, d, J=12 Hz), 3.73-4.06 (5H, m), 7.15-7.25 (2H, m), 7.31-7.38 (3H, m). HPLC purity (retention time): 85% (1.44 min, method C). MS: 271.40 (M+Na$^+$).

Step E: 1-(((3,3-ethylenedioxy-1-phenylcyclohexyl)methoxy)methyl)-3,5-bis(trifluoromethyl) benzene To a solution of ((3,3-ethylenedioxy-1-phenylcyclohexyl) methanol (726 mg, 2.93 mmol) and 3,5-(bis-trifluoromethyl) benzyl bromide (1.08 mL) in DMF (6 mL) at 0° C. was added sodium hydride (95% oil dispersion, 148 mg) and the resulting suspension was stirred at room temperature for 2 hr. Saturated sodium bicarbonate was added to quench the reaction and the organic layer was separated. The aqueous layer was extracted with dichloromethane 3 times and the combined organic layers were dried over magnesium sulfate, filtered and concentrated under vacuum. The crude material was purified by preparative Flash Chromatography eluting with from 10% acetone/90% hexanes to 15% acetone/85% hexanes over 20 minutes to give the title compound as clear pale yellow sticky oil (990 mg, 71% yield). $^1$H NMR (400 MHz, CDCl$_3$) δ 1.25 (1H, m), 1.74 (4H, t, J=8 Hz), 1.90 (1H, d, J=12 Hz), 2.13 (1H, m), 2.24 (1H, d, J=16 Hz), 3.70 (2H, dd, J=8, 36 Hz), 3.91 (4H, m), 4.45 (2H, s), 7.21 (2H, t, J=8 Hz), 7.29-7.38 (4H, m), 7.53 (2H, s), 7.71 (1H, s). HPLC purity (retention time): 100% (2.34 min, method C). MS: 475.14 (M+H$^+$).

Step F: 3-((3,5-bis(trifluoromethyl)benzyloxy)methyl)-3-phenylcyclohexanone

To a solution of 1-(((3,3-ethylenedioxy-1-phenylcyclohexyl)methoxy)methyl)-3,5-bis(trifluoromethyl)benzene (990 mg, 2.09 mmol) in acetone (4 mL) at room temperature were added 1N HCl solution (3.13 mL) and the resulting mixture was stirred at reflux for 2 hr. After cooling down, saturated sodium bicarbonate and dichloromethane were added and the organic layer was separated. The aqueous layer was extracted with dichloromethane 2 times and the combined organic layers were dried over magnesium sulfate, filtered and concentrated under vacuum to give the title compound as clear pale yellow sticky oil (830 mg, 92% yield). $^1$H NMR (400 MHz, CDCl$_3$) δ 1.60 (1H, m), 1.88 (1H, m), 2.19-2.24 (2H, m), 2.29-2.32 (2H, m), 2.85 (2H, dd, J=12, 68 Hz), 3.51 (2H, dd, J=12, 56 Hz), 4.52 (2H, dd, J=16, 18 Hz), 7.22-7.25 (1H, m), 7.32 (4H, d, J=4 Hz), 7.63 (2H, s), 7.77 (1H, s). HPLC purity (retention time): 90% (2.32 min, method C). MS: 453.37 (M+Na$^+$).

Step G: 3-((3,5-bis(trifluoromethyl)benzyloxy)methyl)-N-methyl-3-phenylcyclohexanamine trifluoroacetic acid salt To a solution of 3-((3,5-bis(trifluoromethyl)benzyloxy) methyl)-3-phenylcyclohexanone (10 mg) in methylamine (2.0 M solution in THF, 0.11 mL) at room temperature was added titanium(IV) isopropoxide (0.02 mL) and the resulting solution was heated at 80° C. in a sealed vial for 1.5 h. The solution was cooled to room temperature, 0.1 mL methanol was added followed by sodium borohydride (4.4 mg), and the resulting suspension was stirred at room temperature for 2 h. H$_2$O was added to quench the reaction and the mixture was extracted with dichloromethane 3 times. The combined organic layers were concentrated and residue was purified by preparative HPLC to give the title compound (8 mg, 62% yield). $^1$H NMR (500 MHz, CD$_3$OD) δ 1.39 (1H, m), 1.56 (1H, m), 1.72 (1H, m), 1.88 (1H, m), 2.14 (1H, m), 2.39 (1H, m), 2.61 (1H, m), 2.70 (3H, d, J=25 Hz), 2.71 (1H, m), 3.44 (1H, d, J=5 Hz), 3.79 (2H, dd, J=10, 60 Hz), 4.49-4.60 (2H, m), 7.21-7.28 (1H, m), 7.33 (1H, t, J=8 Hz), 7.38-7.46 (3H, m), 7.65 (1H, s), 7.72 (1H, s), 7.82 (1H, d, J=10 Hz). HPLC purity (retention time): 95% (2.05 min, method C). MS: 446.49 (MH$^+$).

Examples 12-19 were prepared using the general procedure shown in Example 11.

EXAMPLE 12

3-((3,5-bis(trifluoromethyl)benzyloxy)methyl)-N,N-dimethyl-3-phenylcyclohexanamine

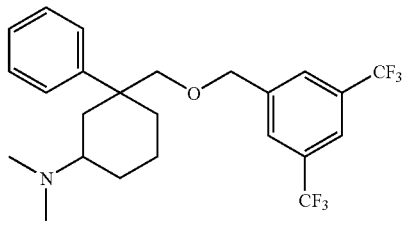

$^1$H NMR (500 MHz, CD$_3$OD) δ 1.58 (1H, m), 1.69 (1H, m), 1.84 (1H, m), 2.06 (1H, m), 2.38 (1H, m), 2.74 (1H, m), 2.88(6H, d, J=25 Hz), 2.88 (2H, s), 3.47 (1H, d, J=5 Hz), 3.70 (2H, dd, J=10, 75 Hz), 4.52 (2H, m), 7.23-7.46 (5H, m), 7.66-7.83 (3H, m). HPLC purity (retention time): 99% (2.16 min, method C). MS: 460.50 (MH+).

EXAMPLE 13

3-((3,5-bis(trifluoromethyl)benzyloxy)methyl)-N,N-diethyl-3-phenylcyclohexanamine

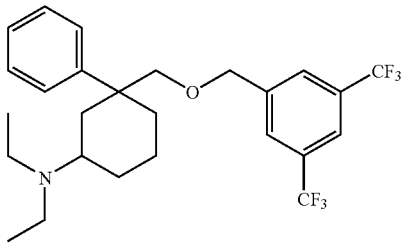

$^1$H NMR (500 MHz, CD$_3$OD) δ 1.27-1.36 (6H, m), 1.56-1.94 (5H, m), 2.09-2.79 (3H, m), 3.07-3.47 (5H, m), 3.71-3.97 (2H, m), 4.49-4.64 (2H, m), 7.23-7.35 (2H, m), 7.39-7.47 (3H, m), 7.69 (2H, dd, J=5, 25 Hz), 7.82 (1H,s). HPLC purity (retention time): 100% (2.19 min, method C). MS: 488.55 (MH+).

EXAMPLE 14

3-((3,5-bis(trifluoromethyl)benzyloxy)methyl)-N-ethyl-3-phenylcyclohexanamine

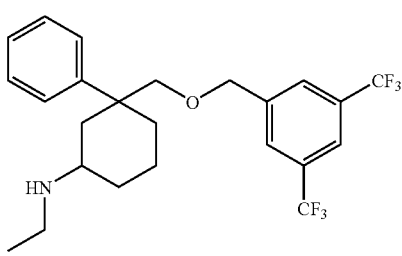

$^1$H NMR (500 MHz, CD$_3$OD) δ 1.26-1.34 (5H, m), 1.51-1.58 (1H, m), 1.67-1.80 (1H, m), 1.91-2.22 (2H, m), 2.28-2.48 (1H, m), 2.72-2.86 (1H, m), 3.05-3.16 (3H, m), 3.45 (1H, d, J=5 Hz), 3.80 (2H, dd, J=10, 65 Hz), 4.48-4.60 (2H, m), 7.21-7.49 (5H, m), 7.69 (2H, d, J=30 Hz), 7.82 (1H, d, J=10 Hz). HPLC purity (retention time): 100% (2.22 min, method C). MS: 460.50 (MH+).

EXAMPLE 15

3-((3,5-bis(trifluoromethyl)benzyloxy)methyl)-N-cyclopropyl-3-phenylcyclohexanamine

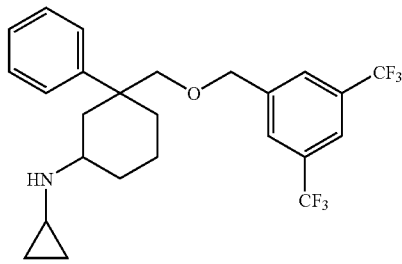

$^1$H NMR (500 MHz, CD$_3$OD) δ 0.80-0.96 (4H, m), 1.35-1.60 (2H, m), 1.67-1.83 (2H, m), 1.92-2.32 (2H, m), 2.46-2.95 (2H, m), 3.16-3.62 (1H, m), 3.45 (1H, d, J=2.5 Hz), 3.82 (2H, dd, J=10, 65 Hz), 4.48-4.61 (2H, m), 7.21-7.34 (2H, m), 7.38-7.47 (3H, m), 7.69 (2H, d, J=30 Hz), 7.82 (1H, d, J=10 Hz). HPLC purity (retention time): 99% (2.16 min, method C). MS: 472.48 (MH+).

EXAMPLE 16

4-(3-((3,5-bis(trifluoromethyl)benzyloxy)methyl)-3-phenylcyclohexyl)morpholine

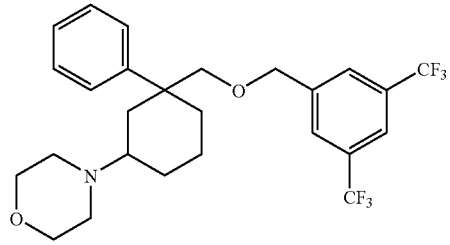

$^1$H NMR (500 MHz, CD$_3$OD) δ 1.45-2.01 (5H, m), 2.07-2.50 (2H, m), 2.78-2.92 (1H, m), 3.12-3.27 (2H, m), 3.38-3.89 (7H, m), 4.08 (2H, d, J=10 Hz), 4.49-4.61 (2H, m), 7.22-7.46 (5H, m), 7.68 (2H, d, J=30 Hz), 7.82 (1H, d, J=10 Hz). HPLC purity (retention time): 100% (2.09 min, method C). MS: 502.54 (MH+).

EXAMPLE 17

1-(3-((3,5-bis(trifluoromethyl)benzyloxy)methyl)-3-phenylcyclohexyl)pyrrolidine

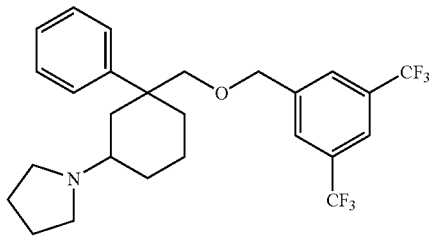

¹H NMR (500 MHz, CD$_3$OD) δ 1.41-1.79 (3H, m), 1.79-2.49 (8H, m), 2.77-2.91 (1H, m), 3.12 (2H, m), 3.45-3.86 (5H, m), 4.50-4.61 (2H, m), 7.22-7.46 (5H, m), 7.70 (2H, d, J=35 Hz), 7.82 (1H, d, J=5 Hz). HPLC purity (retention time): 100% (2.14 min, method C). MS: 486.54 (MH$^+$).

EXAMPLE 18

1-(3-((3,5-bis(trifluoromethyl)benzyloxy)methyl)-3-phenylcyclohexyl)piperidine

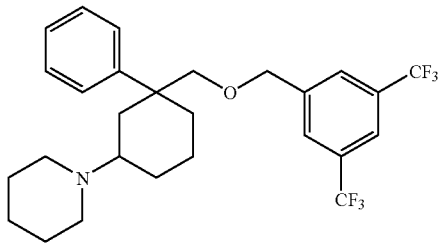

¹H NMR (500 MHz, CD$_3$OD) δ 1.49-2.18 (12H, m), 2.24-2.50 (1H, m), 2.72-2.85 (1H, m), 3.00-3.13 (2H, m), 3.40-3.57 (2H, m), 3.46 (1H, d, J=5 Hz), 3.81 (2H, dd, J=10, 90 Hz), 4.48-4.61 (2H, m), 7.21-7.46 (5H, m), 7.68 (2H, d, J=25 Hz), 7.82 (1H, d, J=5 Hz). HPLC purity (retention time): 100% (2.18 min, method C). MS: 500.53 (MH$^+$).

EXAMPLE 19

1-(3-((3,5-bis(trifluoromethyl)benzyloxy)methyl)-3-phenylcyclohexyl)-4-methylpiperazine

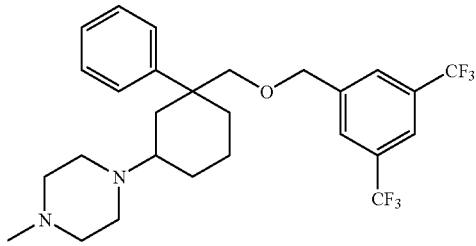

¹H NMR (500 MHz, CD$_3$OD) δ 1.40-1.86 (5H, m), 1.96 (1H, m), 2.14 (1H, m), 2.24 (1H, m), 2.45-3.02 (3H, m), 2.82 (3H, s), 3.31-3.45 (6H, m), 3.80 (2H, dd, J=10, 70 Hz), 4.50-4.59 (2H, m), 7.20-7.45 (5H, m), 7.67 (2H, d, J=30 Hz), 7.81 (1H, d, J=10 Hz). HPLC purity (retention time): 98% (2.03 min, method C). MS: 515.58 (MH$^+$).

HPLC Method A: 4.6×33 mm ODS-A C-18 column, 5 mL/min, 0-100%
MeOH/H2O 0.1% TFA 2 min gradient
HPLC Method C: 3×50 mm ODS-A C-18 column, 5 mL/min, 0-100%
MeOH/H2O 0.1% TFA 3 min gradient
HPLC Method E: 4.6×50 mm XTERRA C18 column, 5 mL/min, 0-100%
MeOH/H2O 0.1% TFA 2 min gradient NK-1 Binding Method U373 cells, a human glioblastoma-astrocytoma cell line that endogenously express the neurokinin-1 (NK-1) receptor, were grown in a monolayer culture at 37° C. in 5% CO$_2$ and fed with Minimum Essential Medium (MEM) supplemented with 10% fetal bovine serum. Membranes were prepared as follows: Cells were washed twice with ice-cold phosphate-buffered saline (pH 7.4) and then incubated for 5 to 10 minutes with ice-cold 10 mM Tris buffer (pH 7.4) containing 5 mM EDTA. Cells were removed from plates, homogenized, and centrifuged at 32,000×g for 20 minutes. The resulting supernatant was discarded, and the pellet resuspended by homogenization in 50 mM Tris buffer (pH 7.4) containing 1 mM EDTA and centrifuged at 32,000×g for 20 minutes. The resulting supernatant was discarded, and the pellet resuspended by homogenization in NK-1 binding assay buffer (50 mM Tris-HCL (pH 7.4), 3 mM MnCl$_2$, 200 µg/ml BSA, 5 µg/ml chymostatin, 40 µg/ml bacitracin and 4 µg/ml leupeptin).

On the day of an experiment the membrane preparation was thawed, homogenized and diluted with NK-1 binding assay buffer to the appropriate concentration. Competition binding assays were performed in 96 well plate format by incubating membranes (5-10 ug/well) with Bolton Hunter labeled [$^{125}$I] Substance P, at a concentration of 200 nM, and concentrations of drugs ranging from 10000 to 0.01 nM. Samples were incubated for 30 min at 20° C. then filtered through GF/B glass fiber filters (pretreated with 1% polyethyleneimine and 0.3% Triton X-100) using a Brandel cell harvester. The filters were then washed with 10 ml ice cold 50 mM Tris-HCL (pH 7.4) containing 3 mM MgCl$_2$. Nonspecific was defined in the presence of 2 µM L-733,060 (a non-peptide NK-1 antagonist). Amount of radioligand bound in the presence and absence of competitor was analyzed by plotting (−)log drug concentration versus the amount of radioligand specifically bound. The midpoint of the displacement curve (IC$_{50}$, nM), signifies the potency. K$_i$ values were calculated using the method of Cheng and Prusoff [Cheng, Y.-C. and Prusoff, W. H., *Biochemical Pharmacology*, Vol. 22, pp. 3099-3108, Pergamon Press (1973)].

NK-1 antagonists have been recognized as useful agents for treating several diseases, e.g.: Chemotherapy-induced nausea and vomiting [Jeremy D. Gale, et al., Expert Opinion on Therapeutic Patents (2001), 11(12), 1837-1847]; Depression [S. Baby, et al., Journal of Clinical Pharmacy and Therapeutics (1999), 24(6), 461-469]; Depression and emesis [Nadia M. Rupniak, et al., Trends in Pharmacological Sciences (1999), 20(12), 485-490]; Treatment of human gliomas [Carla Palma, et al., Life Sciences (2000), 67(9), 985-1001]. Compounds of the present disclosure are NK-1 antagonists and may be useful for the treatment of depression, anxiety, obesity, psychosis, malignant gliomas, or in the control of chemotherapy-induced nausea and vomiting.

Serotonin Transporter Binding Assay

HEK-293 cells that stably express human serotonin transporters (HEK-hSERT cells) were grown at 37° C. in 5% CO$_2$ as a monolayer in medium consisting of EMEM supplemented with 10% fetal bovine serum and G418 sulfate (500 µg/ml). To prepare membranes for radioligand binding experiments, cells were rinsed twice with phosphate-buffered saline (138 mM NaCl, 4.1 mM KCl, 5.1 mM Na$_2$PO$_4$, 1.5 mM KH$_2$O$_4$, 11.1 mM glucose, pH 7.4). Cells were transferred from plates to polypropylene tubes (16×100 mm), centrifuged at 1,200×g for 5 min and were frozen at −80° C. until assay. Following centrifugation, pellets were resuspended by homogenization in buffer consisting of 50 mM Tris (pH 7.7 at 25° C.), 120 mM NaCl and 5 mM KCl and then centrifuged at 32,000×g for 10 min. Following centrifugation, supernatants were discarded and pellets were resuspended in buffer consisting of 50 mM Tris (pH 7.4 at 25° C.), 150 mM NaCl and 5 mM KCl. Membrane homogenates (200 μl/plate) were incubated with 1 nM [$^3$H]-citalopram (specific activity=85 Ci/mmol) and increasing concentrations of test compounds for 1 hr at 25° C. in a total volume of 250 μl. The assay buffer consisted of 50 mM Tris (pH 7.4 at 25° C.), 120 mM NaCl and 5 mM KCl (pH 7.4 with conc. HCl). Plates were incubated for 1 hr at 25° C., then filtered through 0.5% PEI treated Whatman GF/B filters using a Brandel cell harvester. Filters were washed three times with 3 ml of ice-cold tris wash buffer. Non-specific binding was defined with 10 μM fluoxetine. Amount of radioligand bound in the presence and absence of competitor was analyzed by plotting (−)log drug concentration versus the amount of radioligand specifically bound. The midpoint of the displacement curve ($IC_{50}$, nM), signifies the potency. $K_i$ values were calculated using the method of Cheng and Prusoff [Cheng, Y.-C. and Prusoff, W. H., *Biochemical Pharmacology*, Vol. 22, pp. 3099-3108, Pergamon Press (1973)].

NK-1 binding results are shown below in Table I.

TABLE 1

| Example | NK-1 $IC_{50}$ | SERT $IC_{50}$ |
|---|---|---|
| 1 | *** | |
| 2 | *** | |
| 3 | ** | |
| 4 | *** | |
| 5 | *** | |
| 6 | *** | ** |
| 7 | *** | ** |
| 8 | *** | * |
| 9 | *** | ** |
| 10 | *** | *** |
| 11 | *** | * |
| 12 | * | |
| 13 | ** | * |
| 14 | *** | * |
| 15 | ** | |
| 16 | * | |
| 17 | * | |
| 18 | ** | |
| 19 | * | |

*** $IC_{50}$ < 20 nM;
** 20 nM < $IC_{50}$ < 100 nM;
* 100 nM < $IC_{50}$ < 300 nM

As shown in Table 1, the compounds of Example 6, 7, 8, 9, 10, 11, 13 and 14 have activity for both NK-1 and SERT.

What is claimed is:

1. A compound of Formula (I)

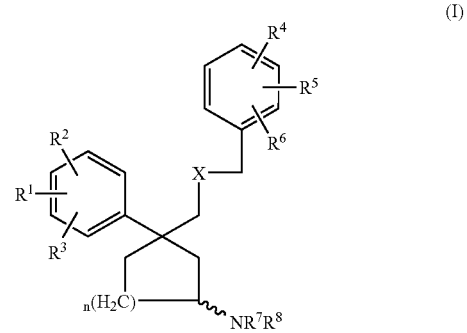

or an isomer, a pharmaceutically acceptable salt or solvate thereof wherein $R^1$, $R^2$, $R^3$, $R^4$, $R^5$ and $R^6$ are independently H, $C_{1-4}$ alkyl, $C_{1-4}$ alkoxy, fluoro $C_{1-4}$ alkyl, halo or cyano;

n is an integer from 1 to 2;

X is O, S or $NR^9$;

$R^7$ and $R^8$ each are independently H, $C_{1-5}$ alkyl, $C_{1-4}$ alkoxy $C_{1-4}$ alkyl, $C_{3-6}$ cycloalkyl, or $C_{3-6}$ cycloalkylmethyl; or $R^7$ and $R^8$ together with the nitrogen to which they are attached form a cyclic ring selected from pyrrolidine, piperidine, homopiperidine, piperazine and N-methyl piperazine; and $R^9$ is H or $C_{1-4}$ alkyl.

2. The compound of claim 1, wherein X is oxygen.

3. The compound of claim 1 wherein $R^4$ and $R^5$ are each $CF_3$ and $R^6$ is H.

4. The compound of claim 1 where n is 1.

5. The compound of claim 1 wherein $R^7$ is H.

6. The compound of claim 1 wherein $R^7$ and $R^8$ are each hydrogen.

7. The compound of claim 2, wherein $R^4$ and $R^5$ are each $CF_3$ and $R^6$ is H.

8. The compound of claim 7 wherein n is 1.

9. The compound of claim 8 wherein $R^7$ are $R^8$ are each hydrogen.

10. The compound of claim 9 wherein $R^1$, $R^2$ and $R^3$ are each hydrogen.

11. The compound of claim 10 wherein the absolute stereochemistry is 1S,3S.

12. A pharmaceutical composition comprising a compound of claim 1, together with at least one pharmaceutically acceptable excipient.

13. A method for the treatment of depression and/or anxiety which method comprises administration to a patient in need of such treatment a therapeutically effective amount of a compound according to claim 1.

* * * * *